(12) United States Patent
Mei et al.

(10) Patent No.: US 8,642,074 B2
(45) Date of Patent: Feb. 4, 2014

(54) THERMOSENSITIVE LIPOSOMES CONTAINING THERAPEUTIC AGENTS

(75) Inventors: Xingguo Mei, Beijing (CN); Qingwei Jiang, Beijing (CN); Weiping Yu, Clarksville, MD (US)

(73) Assignee: Celsion Corporation, Lawrenceville, NJ (US)

( * ) Notice: Subject to any disclaimer, the term of this patent is extended or adjusted under 35 U.S.C. 154(b) by 217 days.

(21) Appl. No.: 12/741,364

(22) PCT Filed: Nov. 5, 2008

(86) PCT No.: PCT/CN2008/001846
§ 371 (c)(1),
(2), (4) Date: Feb. 11, 2011

(87) PCT Pub. No.: WO2009/062398
PCT Pub. Date: May 22, 2009

(65) Prior Publication Data
US 2011/0200665 A1    Aug. 18, 2011

(30) Foreign Application Priority Data
Nov. 5, 2007    (WO) ............... PCT/CN2007/003128

(51) Int. Cl.
*A61K 9/127*    (2006.01)
*A01N 55/02*    (2006.01)

(52) U.S. Cl.
USPC ......................................... 424/450; 514/492

(58) Field of Classification Search
None
See application file for complete search history.

(56) References Cited

U.S. PATENT DOCUMENTS

| | | |
|---|---|---|
| 3,993,754 A | 11/1976 | Rahman et al. |
| 4,863,739 A | 9/1989 | Perez-Soler et al. |
| 4,952,408 A | 8/1990 | Rahman |
| 6,200,598 B1 | 3/2001 | Needham |
| 6,726,925 B1 * | 4/2004 | Needham ...................... 424/450 |
| 2005/0019266 A1 * | 1/2005 | Unger et al. ............... 424/9.321 |
| 2005/0118249 A1 | 6/2005 | Webb et al. |
| 2007/0224255 A1 | 9/2007 | Moscoso Del Prado et al. |

FOREIGN PATENT DOCUMENTS

| | | |
|---|---|---|
| CA | 2186745 A1 | 10/1995 |
| JP | 5-194192 A | 8/1993 |
| JP | 2002-511312 A | 4/2002 |
| JP | 2002-518317 A | 6/2002 |
| JP | 2007-530639 A | 11/2007 |
| WO | WO 95/26185 A1 | 10/1995 |
| WO | WO 99/52505 A1 | 10/1999 |
| WO | WO 99/65466 A1 | 12/1999 |
| WO | WO 2007/024826 A2 | 3/2007 |

OTHER PUBLICATIONS

Weinstein, J., et al., "Liposomes and local hyperthermia: Selective delivery of methotrexate to heated tumors,", *Science* 204:188-191, American Assn. for the Advancement of Science, United States (1979).

* cited by examiner

*Primary Examiner* — Doug Schultz
(74) *Attorney, Agent, or Firm* — Sterne, Kessler, Goldstein & Fox P.L.L.C.

(57) ABSTRACT

A thermosensitive liposome for the delivery of active agents and a composition thereof are disclosed, wherein the liposome comprises at least one phosphatidylcholine, at least one phosphatidylglycerol and at least one lysolipid, and the gel to liquid phase transition temperature of said liposome is from 39 0° C. to 45° C.

16 Claims, 8 Drawing Sheets

The rehydration particle size of liposome effect by the different mode of freeze and water content of lyo-liposome
(■) 0.5°C/min (□)1.5°C/min (●) >20°C/min

000001

THERMOSENSITIVE LIPOSOMES CONTAINING THERAPEUTIC AGENTS

This application is a U.S. National Stage of International Application Number PCT/CN2008/001846, filed Nov. 5, 2008, which is a continuation-in part of International Application Number PCT/CN2007003128, filed Nov. 5, 2007.

BACKGROUND

Liposomes have been used to deliver a wide variety of therapeutic agents. For example, antitumor agents such as actinomycin (U.S. Pat. No. 3,993,754), anthracyclins (U.S. Pat. No. 4,863,739), and vinca alkaloids (U.S. Pat. No. 4,952,408) have been encapsulated in liposomes. More recently, thermosensitive liposomes containing active agents have been prepared and used to deliver the active agent to specific targets in a subject (U.S. Pat. Nos. 6,200,598 and 6,726,925, and Yatvin et al., Science 204:188 (1979). In use, thermosensitive liposomes are delivered to a subject and a target area in the subject is heated. When the thermosensitive liposome reaches the heated area, it undergoes a gel to liquid phase transition and releases the active agent. The success of this technique requires a liposome with a gel to liquid phase transition temperature within the range of temperatures that are obtainable in the subject.

There remains a need in the art for liposomes formulated to encapsulate a therapeutic agent such as an antitumor agent that can undergo a gel to liquid phase transition at a temperature obtainable in a subject. This need and others are met by the present invention.

SUMMARY OF THE INVENTION

In one embodiment, the present invention provides a thermosensitive liposome. Thermosensitive liposomes of the invention typically comprise at least one phosphatidylcholine, at least one phosphatidylglycerol, and at least one lysolipid. Thermosensitive liposomes of the invention will generally have a gel to liquid phase transition temperature of from about 39.0° C. to about 45° C. Optionally, thermosensitive liposomes of the invention may comprise one or more additional lipid components, for example, may comprise a PEGylated phospholipid. A thermosensitive liposome according to the invention may also comprise one or more active agents, for example, therapeutic agents, imaging agents, diagnostic agents, and combinations thereof.

In particular embodiments, the phosphatidylcholine is dipalmitoylphosphatidylcholine (DPPC), the phosphatidylglycerol is distearoylphosphatidylglycerol (DSPG), and the lysolipid is monostearoylphosphatidylcholine (MSPC) and the thermosensitive liposome comprises a PEGylated phospholipid, for example, PEG-2000 modified distearoylphosphatidylethanolamine (DSPE-PEG2000) or PEG-5000 modified distearoylphosphatidylethanolamine (DSPE-PEG5000). Thermosensitive liposomes of the invention may comprise a phosphatidylcholine, a phosphatidylglycerol, a lysolipid and a PEGylated phospholipid in any ratio so long as the gel to liquid phase transition temperature is in the range of from about 39° C. to about 45° C. Typically, liposomes of the invention may comprise the following ratios of ingredients by weight in the following ranges, a phosphatidylcholine 60-80:a phosphatidylglycerol 6-12:a lysolipid 6-12:a PEGylated phospholipid 4-15:an active agent 1-30. For example, a thermosensitive liposome of the invention may comprise a ratio by weight of DPPC 60-80:DSPG 6-12:MSPC 6-12:DSPE-PEG2000 4-15:active agent 1-30.

Thermosensitive liposomes of the invention may comprise one or more active agents. Any active agent known to those skilled in the art may be used in combination with the thermosensitive liposomes of the invention to deliver the active agent to a selected site in a subject. As used herein, a subject is any mammal, in particular, humans, cats or dogs. In one embodiment, thermosensitive liposomes of the invention comprise one or more anticancer agents. Examples of suitable anticancer agents include, but are not limited to, alkylating agents, antimetabolites, spindle poison plant alkaloids, cytotoxic antitumor antibiotics, anthracycline antibiotics, plant alkaloids, taxol derivatives, topoisomerase inhibitors, monoclonal antibodies or fragments thereof, photosensitizers, kinase inhibitors, anti-tumor enzymes and inhibitors of enzymes, apoptosis inducers, biological response modifiers, anti-hormone retinoids, and platinum containing compounds. In a particular embodiment, thermosensitive liposomes of the invention may comprise a taxane, for example, docetaxel. In another particular embodiment, thermosensitive liposomes of the invention may comprise a platinum compound such as carboplatin or cisploatin.

The present invention also provides pharmaceutical compositions comprising thermosensitive liposomes of the invention comprising an active agent. In such pharmaceutical compositions, thermosensitive liposomes of the invention typically comprise at least one phosphatidylcholine, at least one phosphatidylglycerol, at least one lysolipid, and have a gel to liquid phase transition temperature of from about 39.0° C. to about 45° C. Thermosensitive liposomes for use in pharmaceutical compositions of the invention may further comprise a PEGylated phospholipid.

In one example of a suitable thermosensitive liposome for use in the pharmaceutical compositions of the invention the phosphatidylcholine is dipalmitoylphosphatidylcholine (DPPC), the phosphatidylglycerol is distearoylphosphatidylglycerol (DSPG), and the lysolipid is monostearoylphosphatidylcholine (MSPC) and the thermosensitive liposome comprises a PEGylated phospholipid, for example, PEG-2000 modified distearoylphosphatidylethanolamine (DSPE-PEG2000). Such thermosensitive liposomes of the invention may comprise a phosphatidylcholine, a phosphatidylglycerol, a lysolipid and a PEGylated phospholipid in any ratio so long as the gel to liquid phase transition temperature is in the range of from about 39° C. to about 45° C. Typically, liposomes for use in the pharmaceutical compositions of the invention may comprise the following ratios of ingredients by weight in the following ranges, a phosphatidylcholine 60-80:a phosphatidylglycerol 6-12:a lysolipid 6-12:a PEGylated phospholipid 4-15:an active agent 1-30. For example, a thermosensitive liposome of the invention may comprise a ratio by weight of DPPC 60-80:DSPG 6-12:MSPC 6-12:DSPE-PEG2000 4-15:active agent 1-30.

Any active agent may be included in the pharmaceutical compositions of the invention, for example, therapeutic agents and/or imaging agents. In one embodiment, an active agent may be an anticancer agent. Examples of suitable anticancer agents include, but are not limited to, alkylating agents, antimetabolites, antitumor antibiotics, anthracycline antibiotics; plant alkaloids, taxol derivatives, topoisomerase inhibitors, monoclonal antibodies, photosensitizers, kinase inhibitors, and platinum containing compounds. In a particular embodiment, thermosensitive liposomes of the invention may comprise an anthracycline antibiotic, for example, doc etaxel. In a particular embodiment, thermosensitive liposomes of the invention may comprise a platinum containing compound, for example, carboplatin or cisplatin.

The present invention also provides methods of treating disease in a subject using thermosensitive liposomes of the invention. Such thermosensitive liposomes will typically comprise one or more active agents that can be used to treat the disease. A method of treating a disease in a subject in need thereof according to the invention may comprise administering to the subject a therapeutically effective amount of a pharmaceutical composition comprising a temperature sensitive liposome comprising an active agent, where in the liposome comprises at least one phosphatidylcholine, at least one phosphatidylglycerol, at least one lysolipid, and has a gel to liquid phase transition temperature of from about 39.0° C. to about 45° C. The portion of the subject comprising some or all of the diseased tissue is then heated to a temperature sufficient to cause the gel-liquid transition of the liposome thereby releasing the active agent in close proximity to the diseased tissue. Thermosensitive liposomes for use in the methods of the invention may also comprise a PEGylated phospholipid, for example, DSPE-PEG2000 or DSPE-PEG5000.

In one example of thermosensitive liposomes for use in the methods of the invention, the phosphatidylcholine is dipalmitoylphosphatidylcholine (DPPC), the phosphatidylglycerol is distearoylphosphatidylglycerol (DSPG), and the lysolipid is monostearoylphosphatidylcholine (MSPC). Such thermosensitive liposomes for use in the methods of the invention may comprise a phosphatidylcholine, a phosphatidylglycerol, a lysolipid and a PEGylated phospholipid in any ratio so long as the gel to liquid phase transition temperature is in the range of from about 39° C. to about 45° C. Typically, liposomes for use in the methods of treatment of the invention may comprise the following ratios of ingredients by weight in the following ranges, a phosphatidylcholine 60-80:a phosphatidylglycerol 6-12:a lysolipid 6-12:a PEGylated phospholipid 4-15:an active agent 1-30. For example, a thermosensitive liposome of the invention may comprise a ratio by weight of DPPC 60-80:DSPG 6-12:MSPC 6-12:DSPE-PEG2000 4-15:active agent 1-30.

In one embodiment, the present invention comprises a method of treating cancer in a subject in need thereof comprising administering to the subject a therapeutically effective amount of a pharmaceutical composition comprising a temperature sensitive liposome comprising an anticancer agent, wherein the liposome comprises at least one phosphatidylcholine, at least one phosphatidylglycerol, at least one lysolipid, and has a gel to liquid phase transition temperature of from about 39.0° C. to about 45° C. Examples of suitable anticancer agents include, but are not limited to, alkylating agents, antimetabolites, antitumor antibiotics, anthracycline antibiotics, plant alkaloids, taxol derivatives, topoisomerase inhibitors, monoclonal antibodies, photosensitizers, kinase inhibitors, and platinum containing compounds. In one embodiment, the anticancer agent may be an anthracycline antibiotic, for example, docetaxel. In a particular embodiment, thermosensitive liposomes of the invention may comprise a platinum containing compound, for example, carboplatin or cisplatin.

DETAILED DESCRIPTION OF THE INVENTION

Figure 1:
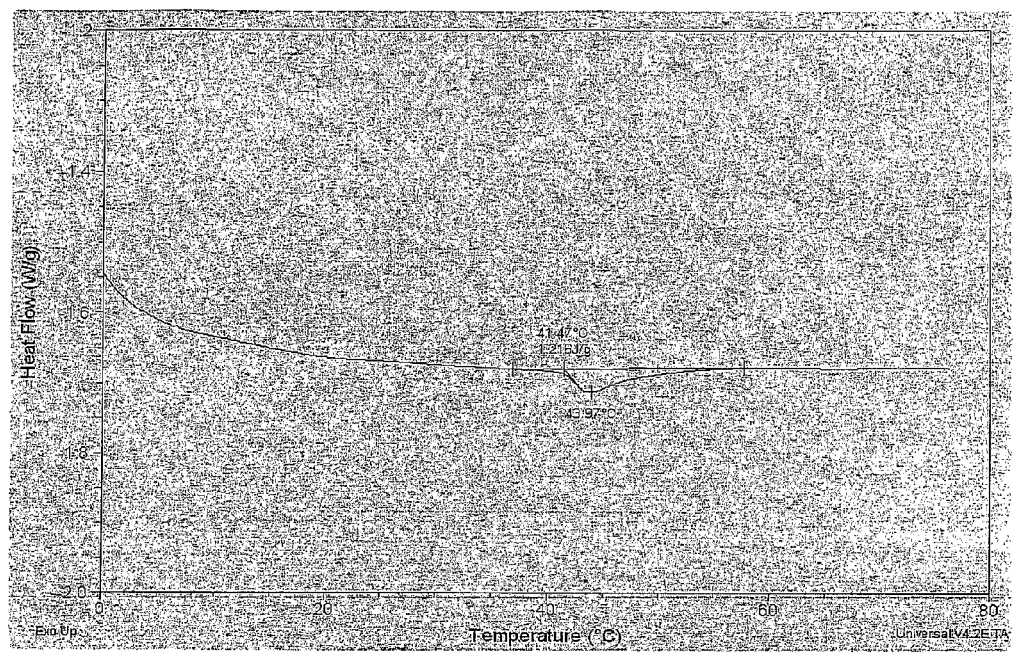
FIG. 1 is a Differential Scanning calorimetry (DSC) trace showing the gel-liquid phase transition of an exemplary thermosensitive liposome of the invention.

Thermosensitive liposomes of the invention typically comprise one or more phosphatidylcholines. Suitable examples of phosphatidylcholines that can be used in the practice of the invention include, but are not limited to, 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine (DPPC), 1,2-Distearoyl-sn-glycero-3-phosphocholine (DSPC), 1,2-Dioleoyl-sn-glycero-3-phosphocholine (DOPC), and 1-Palmitoyl-2-oleoyl-sn-glycero-3-phosphocholine (POPC).

Thermosensitive liposomes of the invention typically comprise one or more phosphatidylglycerols. Suitable examples of phosphatidylglycerols include, but are not limited to, 1,2-Dimyristoyl-sn-glycero-3-phosphoglycerol (DMPG), 1,2-Dipalmitoyl-sn-glycero-3-phosphoglycerol (DPPG), 1,2-Distearoyl-sn-glycero-3-phosphoglycerol (DSPG), and 1-Palmitoyl-2-oleoyl-sn-glycero-3-phosphoglycerol (POPG).

Thermosensitive liposomes of the invention typically comprise one or more lysolipids. As used herein "lysolipid" refers to any derivative of phosphatidic acid (1,2-diacyl-sn glycero-3-phosphate) that contains only one acyl chain covalently linked to the glycerol moiety. Derivatives of phosphatidic acid include, but are not limited to, phosphatidylcholine, phosphatidylglycerol, and phosphatidylethanolamine. Any lysolipid known to those skilled in the art may be used in the practice of the invention.

Thermosensitive liposomes of the invention typically comprise one or more PEGylated phospholipids. Suitable examples of PEGylated phospholipids include, but are not limited to, 1,2-Diacyl-sn-Glycero-3-Phosphoethanolamine-N-[Methoxy(Polyethylene glycol)-350] (mPEG 350 PE), 1,2-Diacyl-sn-Glycero-3-Phosphoethanolamine-N-[Methoxy(Polyethylene glycol)-550] (mPEG 550 PE), 1,2-Diacyl-sn-Glycero-3-Phosphoethanolamine-N-[Methoxy(Polyethylene glycol)-750] (mPEG 750 PE), 1,2-Diacyl-sn-Glycero-3-Phosphoethanolamine-N-[Methoxy(Polyethylene glycol)-1000] (mPEG 1000 PE), 1,2-Diacyl-sn-Glycero-3-Phosphoethanolamine-N-[Methoxy(Polyethylene glycol)-2000] (mPEG 2000 PE), 1,2-Diacyl-sn-Glycero-3-Phosphoethanolamine-N-[Methoxy(Polyethylene glycol)-3000] (mPEG 3000 PE), 1,2-Diacyl-sn-Glycero-3-Phosphoethanolamine-N-[Methoxy(Polyethylene glycol)-5000] (mPEG 5000 PE), PEG-2000 modified distearoylphosphatidylethanolamine (DSPE-PEG2000), and PEG-5000 modified distearoylphosphatidylethanolamine (DSPE-PEG5000).

Active Agents

Thermosensitive liposomes of the invention may be formulated to comprise one or more active agent. As used herein, "active agent" includes any compound desired to be delivered to a specific site in a subject. Any active agent may be used in the practice of the invention.

Anticancer agents may be used as the active agents in the thermosensitive liposomes of the invention. Suitable examples of anticancer agents include:

alkylating agents, for example, nitrogen mustards (e.g., Chlorambucil, Chlormethine, Cyclophosphamide, Ifosfamide, Melphalan, nitrosoureas (e.g., Carmustine, Fotemustine, Lomustine, Streptozocin), platinum containing compounds (e.g., Carboplatin, Cisplatin, Oxaliplatin, BBR3464), Busulfan, Dacarbazine, Mechlorethamine, Procarbazine, Temozolomide, ThioTEPA, and Uramustine;

antimetabolites that target, for example, folic acid (e.g., aminopterin, methotrexate, pemetrexed, raltitrexed), purine metabolism (e.g., cladribine, clofarabine, fludarabine, mercaptopurine, pentostatin, thioguanine), pyrimidine metabolism (e.g., capecitabine, cytarabine, fluorouracil, floxuridine, gemcitabine);

spindle poison plant alkaloids, for example, taxanes (e.g., docetaxel, paclitaxel) and vinca (e.g., vinblastine, vincristine, vindesine, vinorelbine);

cytotoxic/antitumor antibiotics, for example, anthracycline antibiotics (e.g., daunorubicin, doxorubicin, epirubicin, idarubicin, mitoxantrone, valrubicin, carinomycin, nacetylachiamycin, rubidazone, 5-imidodaunomycin, N30 acetyldaunomycin, and epirubicin), bleomycin, mitomycin, and actinomycin;

topoisomerase inhibitors, for example, camptothecines (e.g., camptothecin, topotecan, irinotecan), podophyllum (e.g., etoposide, teniposide).

monoclonal antibodies or fragments thereof, for example, Alemtuzumab, Bevacizumab, Cetuximab, Gemtuzumab, Panitumumab, Rituximab, Tositumomab, and Trastuzumab;

photosensitizers, for example, aminolevulinic acid, methyl aminolevulinate, porfimer sodium, and verteporfin;

kinase inhibitors, for example, Dasatinib, Erlotinib, Gefitinib, Imatinib, Lapatinib, Nilotinib, Sorafenib, Sunitinib, and Vandetanib;

enzymes, for example, asparaginase, pegaspargase and inhibitors of enzymes, for example hydroxyurea;

apoptosis-inducers, for example, arsenic trioxide, Velcade and Genasense;

biological response modifiers, for example, Denileukin Diftitox;

anti-hormones, for example, Goserelin acetate, leuprolide acetate, triptorelin pamoate, Megestrol acetate, Tamoxiifen, toremifene, Fulvestrant, testolactone, anastrozole, exemestane and letrozole; and Retinoids, for example, 9-cis-retinoic acid and all-trans-retinoic acid.

In additional embodiments, the thermosensitive liposomes of the invention can comprise more than one antineoplastic agent, or more than one thermosensitive liposome can be used in the methods of the invention, each of which comprises different active agents, for example, different anticancer agents.

Additional active agents that can be used in the practice of the present invention include, but are not limited to antibiotics, antifungals, anti-inflammatory agents, immunosuppressive agents, anti-infective agents, antivirals, antihelminthic, and antiparasitic compounds.

The thermosensitive liposome of the invention comprising an active agent may comprise the lipids and active agent in any ratio so long as the liposome remains thermally sensitive and can release the active agent at a suitable temperature, for example, between 39° C. and 45° C. Suitable ranges of ratios by weight of a phosphatidylcholine: a phosphatidylglycerol: a lysolipid: a PEGylated phospholipid: an active agent are 60-80:6-12:6-12:4-15: 1-30. Examples of suitable ratios by weight of a phosphatidylcholine: a phosphatidylglycerol: a lysolipid: a PEGylated phospholipid: an active agent, include, but are not limited to, 70:8:8:8:4, 71:8:8:8:4, 72:8:8:8:4, 73:8:8:8:4, 74:8:8:8:4, 75:8:8:8:4, 70:8:8:6:4, 71:8:8:6:4, 72:8:8:6:4, 73:8:8:6:4, 74:8:8:6:4, 75:8:8:6:4, 70:8:8:4:4, 71:8:8:4:4, 72:8:8:4:4, 73:8:8:4:4, 74:8:8:4:4, 75:8:8:4:4, 70:9:9:8:4, 71:9:9:8:4, 72:9:9:8:4, 73:9:9:8:4, 74:9:9:8:4, 75:9:9:8:4, 70:9:9:6:4,.71:9:9:6:4, 72:9:9:6:4, 73:9:9:6:4, 74:9:9:6:4, 75:9:9:6:4, 70:9:9:4:4, 71:9:9:4:4, 72:9:9:4:4, 73:9:9:4:4, 74:9:9:4:4, and 75:9:9:4:4.

Methods of Use

Thermosensitive liposomes of the invention can be administered to a subject using any suitable route, for example, intravenous administration, intraarterial administration, intramuscular administration, intraperitoneal administration, subcutaneous, intradermal intraarticular, intrathecal intracerebroventricular, nasal spray, pulmonary inhalation, oral dministration as well as other suitable routes of administration known to those skilled in the art. Tissues which can be treating using the methods of the present invention include, but are not limited to, nasal, pulmonary, liver, kidney, bone, soft tissue, muscle, adrenal tissue and breast. Tissues that can be treated include both cancerous tissue, otherwise diseased or compromised tissue, as well as healthy tissue if so desired. Any tissue or bodily fluid that can be heated to a temperature above 39.5° C. may be treated with the liposomes of the invention.

The dose of active agent administered to the subject using the thermosensitive liposomes of the invention is readily determined by those of skill in the art, and suitably is administered intravenously over an extended time period, for example over about 1 minute to several hours, for example, 2, 3, 4, 6, 24 or more hours. As used herein "about" indicates a variability of 10% when used to modify a numerical value.

The dose of active agent may be adjusted as is known in the art depending upon the active agent comprised in the carrier.

The target tissue of the subject may be heated before and/or during and/or after administration of the thermosensitive liposomes of the invention. In one embodiment, the target tissue is heated first (for example, for 10 to 30 minutes) and the liposomes of the invention are delivered into the subject as soon after heating as practicable. In another embodiment, thermosensitive liposomes of the invention are delivered to the subject and the target tissue is heated as soon as practicable after the administration.

Any suitable means of heating the target tissue may be used, for example, application of radiofrequency radiation, application of ultrasound which may be high intensity focused ultrasound, application of microwave radiation, any source that generates infrared radiation such as a warm water bath, light, as well as externally or internally applied radiation such as that generated by radioisotopes, electrical and magnetic fields, and/or combinations of the above.

It will be readily apparent to one of ordinary skill in the relevant arts that other suitable modifications and adaptations to the methods and applications described herein can be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Preparation and Characterization of a Thermosensitive Taxotere Liposome

The following materials were used in the preparation of the liposomes of the invention: dipalmitoylphosphatidylcholine (DPPC), distearoylphosphatidylglycerol (DSPG), monostearoylphosphatidylcholine (MSPC), PEGylated distearoylphosphatidylethanolamine (DSPE-mPEG2000), NaCl, KCl, $Na_2HPO_4 \cdot 12H_2O$, $KH_2PO_4$, lactose, $CHCl_3$, methanol, ethanol, and distilled water.

The following equipment was used in the preparation of the liposomes of the invention: water bath, rotary evaporator, homogenizer-extruder, freeze dryer, laser light scattering particle sizer (Smypatec Nanophox), and thermometer.

Method for preparing a 20 ml batch of docetaxel containing liposomes

Measure out the following components in the amounts indicated.

| | Component | | | | |
|---|---|---|---|---|---|
| | DPPC | DSPG | MSPC | DSPE-PEG2000 | Taxotere |
| Quantity | 669 mg | 75 mg | 75 mg | 75 mg | 37.5 mg |

Dissolve above materials with $CHCl_3$/Methanol (3:1) at 55° C. Then remove organic solvent with rotary evaporator. This may be accomplished by rotary evaporation at 55° C. for 1 hour. After drying, nitrogen may be blown over the dried material for a suitable period of time, for example, 5 minutes.

The dried material is then rehydrated. A suitable rehydration solution is phosphate buffered saline (PBS) to which lactose or other stabilizing materials (e.g., sugars) may be added. A suitable protocol for rehydration is to add 20 ml of PBS-5% lactose solution (pH 7.3±0.2) and rotating on the rotary evaporator at atmospheric pressure for 1 hour at 50° C. After rehydration the solution can be degassed under reduced pressure to remove bubbles.

After hydration, the particle size of the liposomes may be adjusted to the desired range, for example, 100±15 mn. A suitable extrusion protocol is to use a homogenizer/extruder with a 200 nm filter and extrude three times. Change to a 100 nm filter and extrude three times. Finally, change to an 80 nm filter and extrude three times. The particle size distribution of the liposomes can be measured using any suitable technique, for example, using Photon Crosscorrelation Spectroscopy (PCCS) and a Nanophox sensor (Sympatec GmbH). After extrusion, the liposomal solution can be sterilized by filtration through a 0.22 μm pore-size membrane filter (Millipore).

After sterilization, the liposome is filled into vial and lyophilized. The lyophilization program is as follows: −50° C. 2 h, −45° C. 1 h, −35° C. 10 h, −15° C. 5 h, 0° C. 2 h, 10° C. 2 h, 20° C. 6 h.

Another suitable method for preparation of the liposomes of the invention is as follows:

Dissolve the same components as above in $CHCl_3$/Methanol (3:1) at 55° C. Remove organic solvent with rotary evaporator as above. Rehydrate with 20 ml of PBS-5% lactose solution at 50° C. as above. Place the rehydrated material in a homogenizer and process at 15,000 psi for 5 minutes to reduce the particle size. Take the homogenized material and use an extruder with a 100 nm filter and extrude six times to reduce particle size to 100±15 nm (100 nm×6) and then sterilize by 0.22 μm filtration. After sterilization, the liposome is filled into vial and lyophilized.

Analytical Methods

Morphology of the liposomes can be analyzed by electron microscopy. Liposomes were negative stained with phosphotungstic acid and transferred to a copper mesh. The water was allowed to evaporate and the samples were observed under the electronic microscope. Liposomes prepared by the methods of the invention were homogeneous when viewed under the electron microscope.

The percentage of drug encapsulated (Encapsulation %) was measured for the liposomes prepared as described above. Encapsulation %=Encapsulated drug/Total drug×100%. The Encapsulation% was determined as follows: 1 ml of the liposome was centrifuged at 6000 rpm for 5 min. The docetaxel in the supernatant was measured by HPLC. The docetaxel content of the liposomes was determined by extracting the docetaxel from the liposomes and measuring the extracted docetaxel by HPLC. For extraction, 0.1 ml of liposome was diluted with water:acetonitrile (45:55) to 0.5 ml. 4 ml tert-butyl methyl ether was added and mixed for 30 seconds. The mixture was centrifuge the mixture at 300 g for 15 min. 3 ml of the organic layer was removed and dried by rotary evaporation. The dried material was resuspended in 200 μl water:acetonitrile (45:55) and 5-10 μl was inject on the HPLC for analysis.

The HPLC analysis was conducted under the following conditions: a Venusil C 18 column (Reverse phase C 18 column) was used with a mobile phase of water:acetonitrile (45:55) at 1 ml/min. Column temperature was 30° C. UV detection was set at 230 nm. Under these conditions, the drug detection limit is between 20 -800 ng.

The ability of the above protocol to recover docetaxel in a sample was determined. To 0.1 ml of liposomes prepared as described above 0.1 ml of docetaxel standard solution was added. The sample was diluted with water:acetonitrile (45:55) to 0.5 ml. 4 ml tert-butyl methyl ether was added and the sample mixed for 30 seconds. The sample is then centrifuged at 300 g for 15 min. 3 ml of the organic layer is dried by rotary evaporation. 200 μl of water:acetonitrile (45:55) is added to the residue and 5-10 μl is then injected on the HPLC. The following table provides the recovery rate at various concentrations of docetaxel.

| Drug conc. | Recovery % | Recovery % | Recovery % | mean |
|---|---|---|---|---|
| 80 μg/ml | 100.34 | 99.97 | 99.41 | 99.91 |
| 100 μg/ml | 99.15 | 96.63 | 98.08 | 97.95 |
| 120 μg/ml | 97.68 | 99.01 | 99.41 | 98.70 |

The phase transition temperature of the liposomes prepared according to the invention was determined. Differential Scanning calorimetry (DSC) measurements were performed using a Q100 (TA Instruments, Inc. New Castle Del.) with empty hermetically sealed aluminum pans as reference. The lipid concentration was made to 20 mg/ml and 10 μl of liposome suspension was carefully placed and sealed in the aluminum hermetic pans. The scan rate was set at 2° C. per minute. FIG. 1 shows a DSC trace obtained with the liposomes of the invention. DSC spectrum shows that the taxotere thermosensitive liposome phase transition temperature is at about 42° C.

The stability of the liposomes prepared by the above methods was assessed by periodically measuring the particle size during storage. The results in the table below show that liposomes prepared as above are stable for at least 3 months.

| | Time | | | |
|---|---|---|---|---|
| | Before lyophilization | After lyophilization | 1 month | 2 month | 3 month |
| Size | 97 nm | 101 nm | 107 nm | 106 nm | 106 nm |

The drug content was monitored also. The results showed that after lyophilization, the liposome is stable at 2-8° C. for at least 3 months.

Drug Content of the Liposome

| | Time | | | |
|---|---|---|---|---|
| | After lyophilization | 1 month | 2 months | 3 months |
| Taxotere (mg/ml) | 1.132 | 1.131 | 1.132 | 1.130 |

The drug encapsulation rate was monitored as well. The results showed that after lyophilization, the amount of drug encapsulated by liposome is stable at 2-8° C. for at least 3 months.

Drug Encapsulation

| | Time | | | |
|---|---|---|---|---|
| | After lyophilization | 1 month | 2 months | 3 months |
| Encapsulation % | 99.0 | 98.6 | 98.1 | 98.3 |

Figure 2:
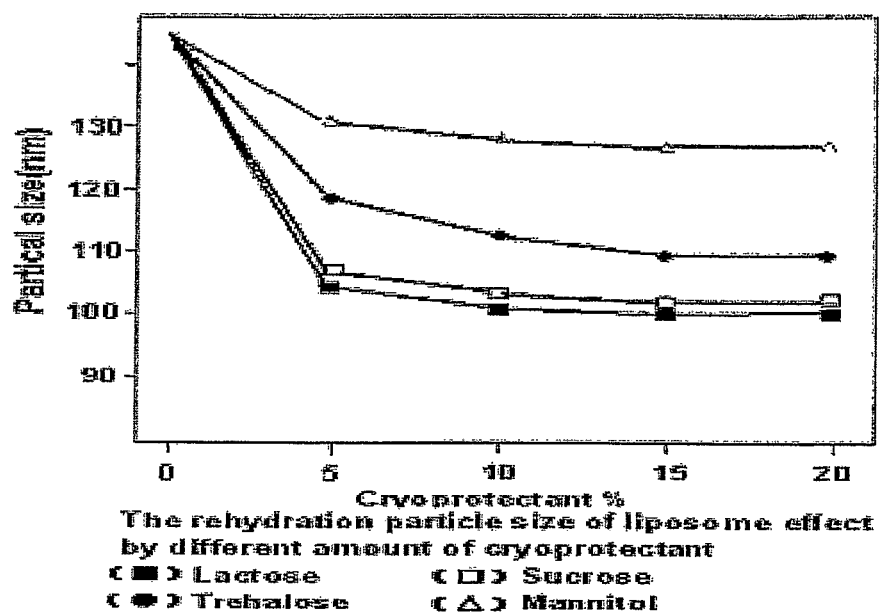
FIG. 2 is a graph of particle size as a function of the amount of cryoprotectant in the liposome preparation lyophilized.

Different cryoprotectants were tested for their effect on particle size during lyophilization. Lactose, trehalose, sucrose and mannitol were tested. The results showed that lactose and sucrose are more effective than mannitol and trehalose. FIG. 2 shows a graph of particle size as a function of the % by weight of cryoprotectant present in the solution lyophilized.

Figure 3:
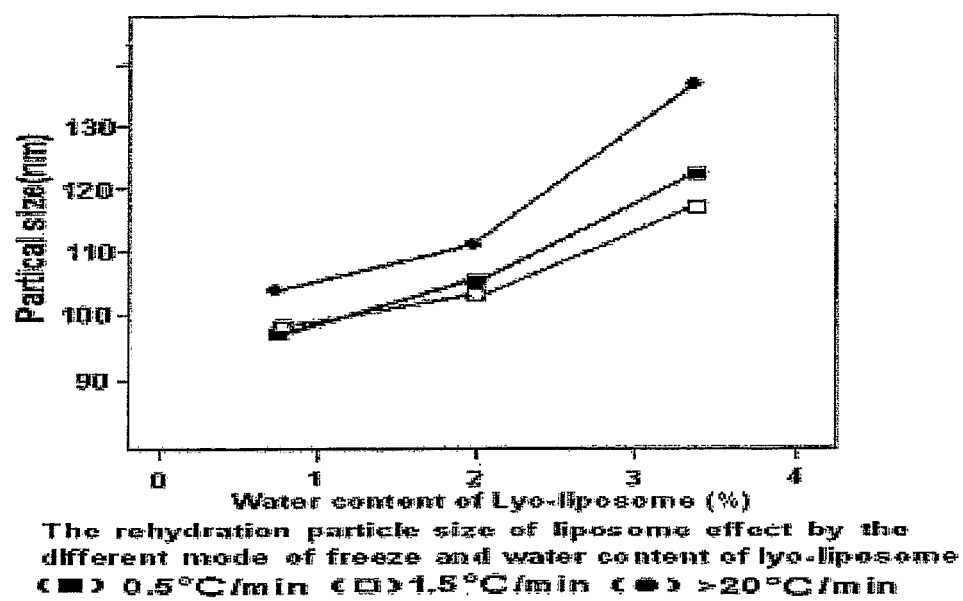
FIG. 3 is a graph of particle size upon rehydration of lyophilized liposomes of the invention as a function of water content of the liposomes at various rates of temperature during freezing.

The rate at which the liposomes are frozen for lyophilization and the water content of the liposomes has an effect on the particle size. FIG. 3 shows a graph of particle size as a function of the water content of the liposomes at three different freezing rates. has an effect on the particle size.

Rehydration media has also impact on the liposome particle size. Water, 5% dextrose in water (D5W) and 0.9% NaCl were tested. 0.9% NaCl and 5% dextrose in water maintain the liposome particle size. The following table shows the results of two different liposome.formations with three independent measurements. The average diameter of the liposomes is provided in nanometers (nm). Formulation F4-1 had the following components DPPC: DSPG: DSPE-PEG: MSPC: Docetaxel at the following weight % 71.56:8.15:8.24: 8.02:4.00 and F4-2 had the same components at 71.78:8.06: 8.10:8.07:3.98 weight %.

| Rehydration Media | Formulation | 1 (nm) | 2 (nm) | 3 (nm) |
|---|---|---|---|---|
| Water | F4-1 | 136 | 133 | 139 |
| | F4-2 | 132 | 128 | 141 |
| D5W | F4-1 | 97 | 101 | 103 |
| | F4-2 | 102 | 104 | 105 |
| 0.9% NaCl | F4-1 | 101 | 105 | 102 |
| | F4-2 | 106 | 103 | 101 |

Figure 4A:
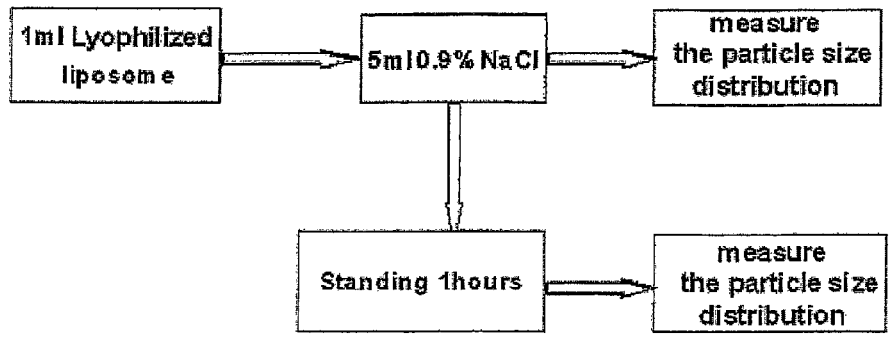
FIG. 4A is a schematic of the protocol used to test the effects of standing on particle size of rehydrated liposomes of the invention.
Figure 4B:
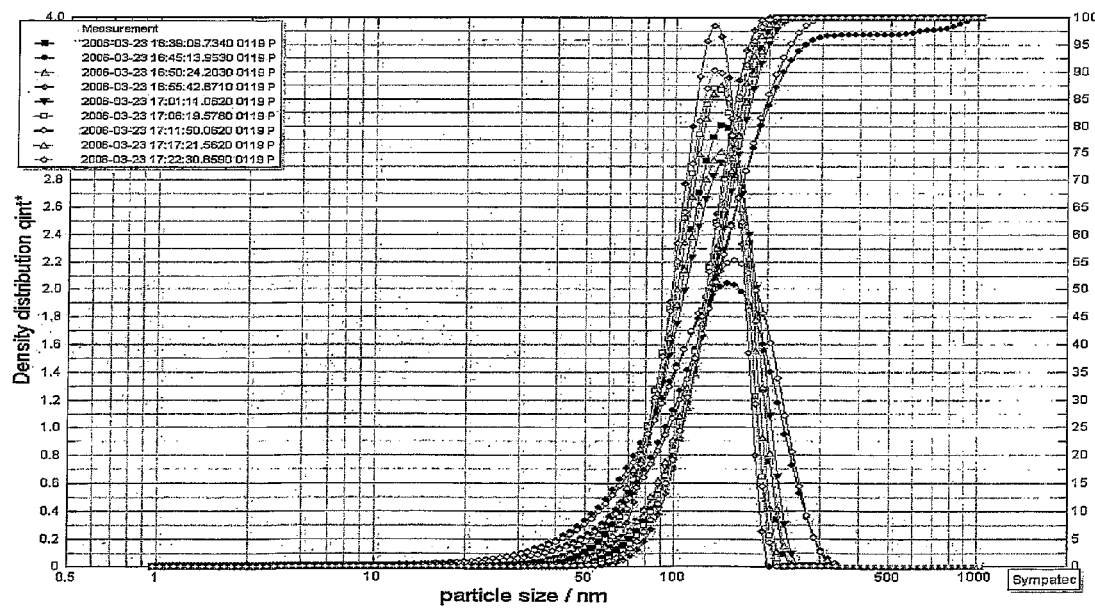
FIG. 4B is a graph showing the particle size distribution of rehydrated liposomes of the invention over a one hour time period.

The stability of the liposomes after rehydration was examined. The lyophilized liposomes were rehydrated with 0.9% NaCl and tested as shown schematically in FIG. 4A. The particle size distribution was monitored with dynamic light scattering apparatus by repeated scans over a period of 1 hour. The results show that the particle distribution of rehydrated liposome is stable for 1 hour (FIG. 4B).

The lyophilized liposomes were stored at various temperatures for 9 months.

The liposomes were tested at 0, 1., 3, 6 and 9 months for encapsulation % and average particle size were tested. The results in the following table show that liposomes were stable up to 9 months at 4° C.

| Storage time (month) | Storage temperature −20° C. | Storage temperature 4° C. | Storage temperature 20° C. |
|---|---|---|---|
| 0 | 92.1% (98 nm) | 92.1% (98 nm) | 92.1% (98 nm) |
| 1 | 91.8% (101 nm) | 91.5% (103 nm) | 91.7% (107 nm) |
| 2 | 91.6% (102 nm) | 91.4% (105 nm) | 91.1% (106 nm) |
| 3 | 91.5% (105 nm) | 91.2% (106 nm) | 90.8% (109 nm) |
| 6 | 91.4% (108 nm) | 91.3% (107 nm) | 90.9% (111 nm) |
| 9 | 90.8% (112 nm) | 90.5% (110 nm) | 90.2% (116 nm) |

Example 2

In vivo drug distribution obtained with the liposomes of the invention compared to that obtained with free docetaxel.

Six female BALB/c mice (20±2 g) were randomly separated into 3 groups. The mice were anesthetized and put on a Styrofoam board with a hole in it. One leg of the mouse was pulled through the hole to other side of the board. The board was floated in a water bath to heat the leg at 43.5±0.5° C. for 15 min. The mice then received a tail vein injection of either liposomes at a dose of 10 mg/kg or the same dose of Taxotere (control: prepared according to the manufacturers specifications) The one leg from each mouse was then heated for 30 min. after injection and then sacrificed. Muscles from the heated and non-heated legs were excised. Drug was extracted from a fixed weight of muscle tissue using the extraction method described above. The extracted drug was analyzed by HPLC. The results are shown in following table.

|  | Docetaxel Liposome | | Docetaxel | |
|---|---|---|---|---|
|  | $A_{drug}/A_{ref}$% (heated leg) | $A_{drug}/A_{ref}$% (non-heated leg) | $A_{drug}/A_{ref}$% (heated leg) | $A_{drug}/A_{ref}$% (non-heated leg) |
| Group 1 | 13.3 | 4.9 | 5.46 | 5.48 |
| Group 2 | 14.3 | 5.60 | 6.53 | 6.29 |
| Group 3 | 11.1 | 5.69 | 5.48 | 5.32 |

The data show that the temperature sensitive liposome delivered more that twice as much docetaxel to the heated leg than to the non-heated leg.

Example 3

In vivo drug distribution obtained with the liposomes of the invention compared to that obtained with non-thermosensitive docetaxel-containing liposome The thermosensitive liposomes and non thermosensitive liposomes were made according to the formula shown in the following table:

| Composition | Docetaxel | DPPC | DSPG | PEG-DSPE | MSPC |
|---|---|---|---|---|---|
| Thermosensitive | 25 mg | 450 mg | 50 mg | 50 mg | 50 mg |
| Non-thermosensitive | 25 mg | 450 mg | 50 mg | 50 mg | 0 |

Six female BALB/c mice (20±2 g) were randomly separated into 3 groups. The mice were anesthetized and put on a Styrofoam board with a hole in it. One leg of the mouse was pulled through the hole to other side of the board. The board was floated in a water bath to heat the leg at 43.5±0.5° C. for 15 min. The mice then received a tail vein injection of either liposomes at a dose of 10 mg/kg or the same dose of Taxotere (control: prepared according to the manufacturers specifications) The one leg from each mouse was then heated for 30 min. after injection and then sacrificed. Muscles from the heated and non-heated legs were excised. Drug was extracted from a fixed weight of muscle tissue using the extraction method described above. The extracted drug was analyzed by HPLC. The results are shown in following table.

|  | Group | | | |
|---|---|---|---|---|
|  | Thermosensitive Liposome | | Non thermosensitive liposome | |
| Heat/No heat | Heated | Non heated | Heated | Non heated |
| $A_{drug}/A_{ref}$% | 0.704 | 0.428 | 0.443 | 0.444 |

In the thermosensitive liposome group, drug concentration in heated tissue is about 2 times higher than non heated tissue. In docetaxel injection (Example 2) and non thermosensitive liposome groups, the drug concentration is the same in the heated and non heated tissue. These results showed that theimosensitive liposome did released the drug into the tissues under these experimental conditions.

Example 4

The in vivo efficacy of docetaxel delivery using the liposomes of the invention compared to that of free docetaxel in mice bearing Lewis lung tumors.

Twelve female Kunming mice, between 7-9 weeks old and weighing 20±2 g were used. Lewis lung carcinoma cells ($3 \times 10^6$ cells in 0.1 ml of PBS.) were implanted subcutaneously into the right lower leg of each mouse. Tumors were allowed to grow to 4-6 mm in diameter before starting treatment.

The 12 mice were stratified by tumor volume and randomized to 3 treatment groups: saline, free docetaxel and the thermosensitive liposomes of the invention.

| Group | Animals/Group | Treatment | Dose (mg/m$^2$) | Heating time (mins) |
|---|---|---|---|---|
| 1 | 2 | Saline | 0 | 30 |
| 2 | 4 | Docetaxel injection | 75 | 30 |
| 3 | 6 | Docetaxel Thermosensitive Liposome | 75 | 30 |

Docetaxel-containing thermosensitive liposomes of the invention were prepared as described above and stored at 2-8° C. until use. Treated animals were injected with 75 mg/m$^2$ docetaxel either in a thermosensitive liposome of the invention or as non-liposomal Taxotere prepared according to the manufacturer's specifications.

The treatment was started on day 8 after the tumor implantation and was repeated on day 12 and day 16. Mice in all treatment groups were anesthetized with an IP injection of pentobarbital (80 mg/kg); treatment was administered in a volume of 0.2 ml via tail vein injection. This dose of anesthesia provided adequate immobilization for the 1-h treatment period.

Except for the saline group, all treatment groups were given an equivalent dose of 75 mg/m$^2$ of docetaxel. Immediately after injection, the mice were positioned in specially designed holders that allowed the isolated leg tumor to be placed in a water bath for 30 minutes. The water bath temperature was set at 43° C. This water bath temperature has been calibrated previously to give tumor temperatures of 42° C. All the mice were sacrificed at day 18. The tumors were surgically excised and the tumor weights were recorded. The tumor growth inhibition was calculated as follows:

Tumor Inhibition Ratio=$(Vs-Vx)/Vs$

Where: Vs is tumor volume of saline group, Vx is the tumor volume of treatment group.

The results are shown in the following table.

| Group | Mice No | Tumor Weight | Average | Inhibition % |
|---|---|---|---|---|
| Saline | 1 | 5.874 | 4.537 | 0 |
|  | 2 | 3.199 |  |  |
| Docetaxel Injection | 3 | 0.500 | 1.002 | 77.91 |
|  | 4 | 0.118 |  |  |
|  | 5 | 1.380 |  |  |
|  | 6 | 2.010 |  |  |
| Docetaxel Thermosensitive Liposome | 7 | 0.031 | 0.0785 | 98.27 |
|  | 8 | 0.009 |  |  |
|  | 9 | 0.078 |  |  |
|  | 10 | 0.152 |  |  |
|  | 11 | 0.151 |  |  |
|  | 12 | 0.050 |  |  |

Delivering docetaxel in a thermosensitive liposome formulation and local heating of the tumor resulted in greater tumor inhibition than delivery of docetaxel alone. In two mice treated with thermosensitive liposome, the tumors almost disappeared.

Example 5

Preparation of a Thermosensitive Liposome Containing Carboplatin

Liposomes may be prepared using any technique known to those skilled in the art. One suitable technique is as follows.

The liposomes were made with lipids listed in the following table.

| Lipids | Weight (mg) |
| --- | --- |
| DPPC | 2000 |
| MSPC | 150 |
| DSPG | 250 |
| DSPE-mPEG | 250 |

Dissolve the lipids in 3 ml of chloroform. Rotary evaporate the chloroform at 60° C. at reduced pressure to form a thin film. Continue heat for 40 minutes to remove organic solvent. Add 25 ml water to hydrate the dried lipid film at 60° C. for 10 minutes. Reduce pressure at room temperature to remove air bubbles for 10 minutes. Heat for another 10 minutes at 60° C. Extrude the lipid suspension through a 200 nm membrane 10 times. Extrude through a 100 nm membrane 4 times. The liposomes thus prepared may be stored at 4° C.

The liposomes may then be loaded with an active agent, for example, with carboplatin, using any suitable technique known in the art. One suitable technique is as follows:

Add 800 mg carboplatin and 1000 mg lactose into 20 ml of empty liposomes at 106 mg liposomes/ml. Heat the mixture at 60° C. in a water bath and stir at 300 r/min, for 30 minutes. The loaded liposomes may be stored at 4° C.

The excess drug may be removed from the loaded liposomes using any technique known in the art, for example, size exclusion chromatography or dialysis. One suitable techniques is a follows:

The loaded liposome solution may be put into a dialysis bag (molecular cut off: 8000-14000). The solution may be dialysis the liposome with 200 ml of 5% lactose solution at 4° C. for 2 hours. Replace the dialysis solution with fresh 200 ml 5% lactose solution and dialysis for another 2 hours at 4° C. The loaded liposomes may be removed from the dialysis bag and stored at 4° C. Loaded liposomes should be protected from exposure to light.

Example 6

Physical Characterization of Carboplatin-Containing Liposomes

Figure 5:
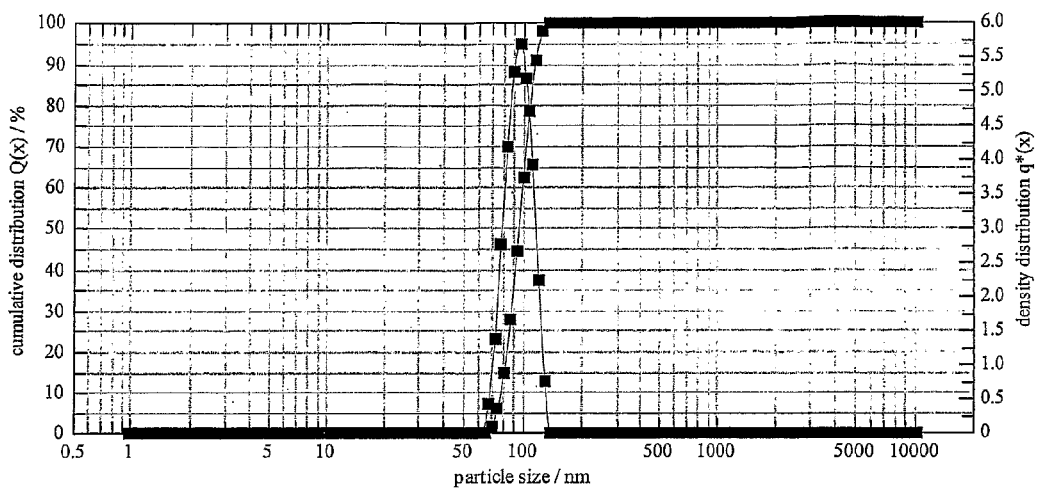
FIG. 5 is a line graph of the particle size distribution of thermosensitive carboplatin liposomes.
Figure 6:
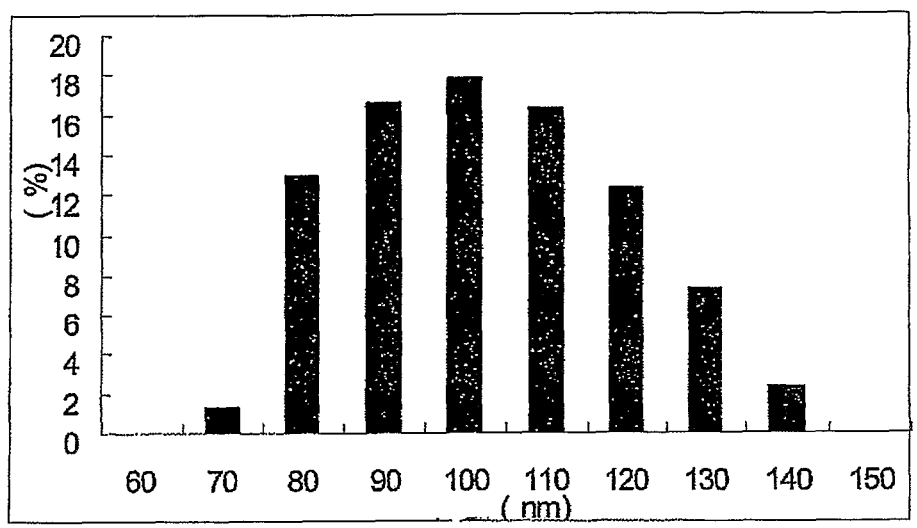
FIG. 6 is a bar graph of the particle size distribution of thermosensitive carboplatin liposomes.

After separation of drug loaded liposome from free drug, the liposome has a drug/lipids ratio at 0.04 as seen in the following table and an average particle size of 95 nm (FIGS. 5 and 6). The concentration of lipids is 106 mg/ml.

| Liposome Particle Size | Total Drug | Free Drug | Encapsulation % | Drug/Lipids |
| --- | --- | --- | --- | --- |
| 100 nm | 4.63 mg/ml | 0.0 mg/ml | 100% | 0.04 |

Since carboplatin liposome needs to be diluted in clinical application, the stability of carboplatin-containing liposomes of the invention was tested using a 5% glucose solution and water as diluents. The liposome stability in these diluents was tested by diluting. 10 µl of the liposome with 990 µl of the diluents, at room temperature for 6 hours. The drug leakage after dilution was analyzed by comparing drug encapsulation before and after dilution. The following table shows the results obtained. The data showed that the carboplatin liposome is compatible with either water or 5% glucose.

| Diluents | Drug leakage | Average |
| --- | --- | --- |
| 5% Glucose | 0.23% | 0.19% |
| | 0.23% | |
| | 0.12% | |
| Water | −0.35% | −0.08% |
| | 0.00% | |
| | 0.12% | |

Example 7

Characterization of the Drug Release Profile of Carboplatin-Containing Liposomes The carboplatin drug release profile was analyzed at 37° C. and 42° C. The detailed method is as follows:

Water baths were equilibrated to 38° C. and 43° C. respectively (the test sample temperature is 1 degree lower than water bath). 1.0 ml aliquots of liposome were diluted into 9.0 ml of a 5% glucose solution. 5 ml of the diluted solution was heated in the 38° C. water bath. The remaining 5 ml of the diluted solution was heated in the 43° C. water bath. At various time points after heating is initiated, 200 µl samples from each temperature were taken. Samples were taken at 0, 0.25, 0.5, 1, 2, 4, 8, 16, 32, 64 and 128 min for 42° C. sample, and 0, 2, 8, 32 and 128 min for 37° C. sample. The samples were cooled down in ice water immediately after taking.

The samples were analyzed for total drug and free drug concentration. The drug released was calculated by following equation:

Drug Release=$C$ free/$C$ total×100%

Figure 7:
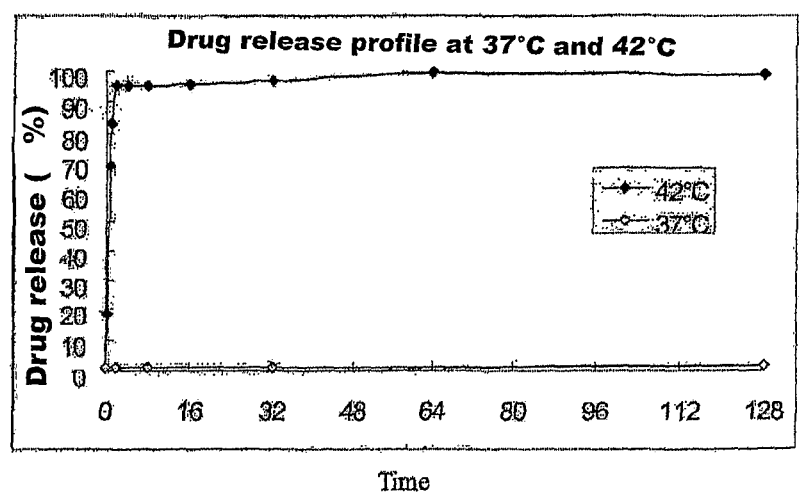
FIG. 7 is a line graph of the drug release at 37° C. (open diamonds) and 42° C. (filled diamonds) as a function of time.

The following table and FIG. 7 show the results obtained.

| Time (min) | 0 | 0.25 | 0.5 | 1 | 2 | 4 | 8 | 16 | 32 | 64 | 128 |
| --- | --- | --- | --- | --- | --- | --- | --- | --- | --- | --- | --- |
| 42° C. (%) | 0.9 | 18.5 | 69.3 | 83.2 | 95.3 | 95.3 | 95.3 | 95.8 | 97.0 | 99.5 | 99.0 |
| 37° C. (%) | 0.9 | | | | 0.8 | | 0.9 | | 1.0 | | 1.9 |

These data indicate that the liposomes of the invention release drug rapidly after heating.

Figure 8:
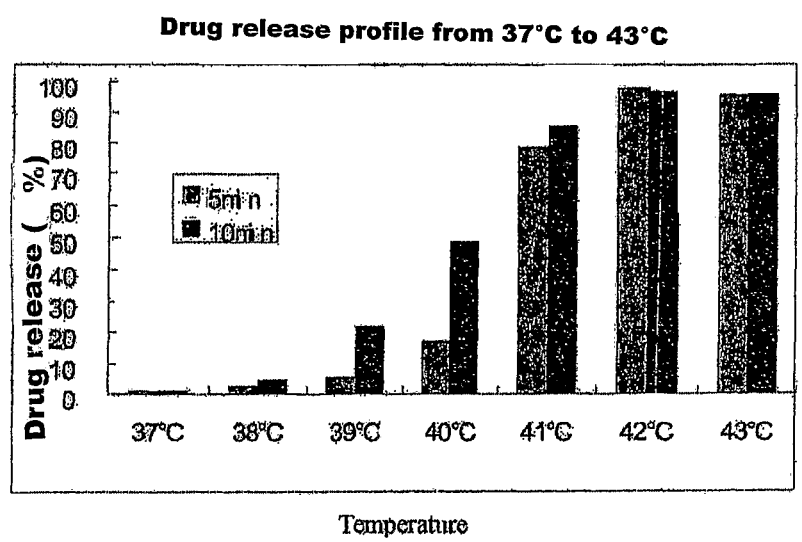
FIG. 8 is a bar graph showing release of carboplatin at various temperatures at 5 minutes (blue) and 10 minutes (magenta).

To further characterize the drug release profile of the liposomes of the invention, the drug release of carboplatin-containing liposomes was also tested at various temperatures from 37° C. to 43° C. at 5 and 10 minutes of heating. The following table and FIG. 8 show the % of drug released. At 37° C., there is almost no drug release, while starting at 40° C., drug releases rapidly.

| | Temperature (° C.) | | | | | | |
|---|---|---|---|---|---|---|---|
| | 37 | 38 | 39 | 40 | 41 | 42 | 43 |
| 5 min | 0.9% | 2.6% | 5.6% | 17.4% | 78.5% | 98.2% | 95.4% |
| 10 min | 0.9% | 4.6% | 21.8% | 48.7% | 85.5% | 96.6% | 95.8% |

Example 8

Characterization of the Stability of Carboplatin-Containing Liposomes

The drug leakage during storage at different temperatures was evaluated.

The liposomes were stored at −20° C., 4° C. and 25° C. for 5 or 10 days. The encapsulation % of the drug was analyzed. The results presented in the following table show that the liposomes of the invention are stable at 4° C. for 10 days.

| | Temperature | | | |
|---|---|---|---|---|
| | 4° C. | | 25° C. | |
| Time (day) | 5 | 10 | 5 | 10 |
| Leakage | 0.01% | 0.01% | 1.55% | 2.52% |

To determine if the liposomes of the invention can be sterilized by filtration, their stability to filtration was analyzed. 2 ml aliquots of liposome were filtered through a 0.22 µm filter. The % of drug encapsulated was analyzed before and after filtration. The data in the following table show that the liposome can be filtered at small volume.

| | Before filtration | After filtration |
|---|---|---|
| Leakage (%) | 0% | 0.62% |

The long term stability of the liposomes was assessed by storing the liposomes at 4° C. The drug leakage was evaluated at 0, 1, and 2 months. As shown in the following table, the liposomes of the invention are stable at 4° C. for at least 6 months.

| Time (month) | Drug content | Leakage | Particle Size |
|---|---|---|---|
| 0 | 4.63 mg/mL | 0.00% | 99.79 nm |
| 1 | 4.60 mg/mL | 0.03% | 106.01 nm |
| 2 | 4.62 mg/mL | 0.09% | 99.24 nm |
| 3 | 4.59 mg/mL | 0.14% | 101.78 nm |
| 6 | 4.60 mg/mL | 0.24% | 100.09 nm |

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A thermosensitive liposome comprising dipalmitoylphosphatidylcholine (DPPC), distearoylphosphatidylglycerol (DSPG), monostearoylphosphatidylcholine (MSPC), PEG-2000 modified distearoylphosphatidylethanolamine (DSPE-PEG2000), and an active agent, at a ratio of about 60-80:6-12:6-12:4-15:1-30 on a weight basis, wherein the liposome has a gel to liquid phase transition temperature of from about 39.0° C. to about 45° C.

2. A thermosensitive liposome according to claim 1, wherein the active agent, is an anticancer agent.

3. A thermosensitive liposome according to claim 2, wherein the anticancer agent is selected from the group consisting of alkylating agents, antimetabolites, spindle poison plant alkaloids, cytotoxic antitumor antibiotics, topoisomerase inhibitors, monoclonal antibodies or fragments thereof, photosensitizers, kinase inhibitors, antitumor enzymes and inhibitors of enzymes, apoptosis-inducers, biological response modifiers, anti-hormones, retinoids, nucleoside analogs and platinum containing compounds.

4. A thermosensitive liposome according to claim 2, wherein the anticancer agent is a taxane.

5. A thermosensitive liposome according to claim 4, wherein the taxane is docetaxel or paclitaxel.

6. A thermosensitive liposome according to claim 3, wherein the anticancer agent is a platinum containing compound.

7. A thermosensitive liposome according to claim 6, wherein the platinum containing compound is carboplatin or cisplatin.

8. A thermosensitive liposome according to claim 3, wherein the anticancer agent is the nucleoside analog gemcitabine.

9. A pharmaceutical composition comprising a thermosensitive liposome of claim 1.

10. The composition of claim 9, wherein the active agent is docetaxel, and both the liposome particle size and amount of docetaxel retained within the liposome remain substantially stable when said composition is stored at 2-8° C. for 1 to 9 months.

11. The composition of claim 9, wherein the active agent is carboplatin, and amount of carboplatin retained within the liposome remains substantially stable when said composition is stored at 4° C. for 1 to 6 months.

12. The composition of claim 9, wherein the active agent is carboplatin, and at least 83.2% of the carboplatin is released from the liposomes when the liposomes are heated from 1-128 minutes at 42° C.

13. A method of treating a disease in a subject in need thereof, comprising: administering to the subject a therapeutically effective amount of a pharmaceutical composition of claim 9; and heating an area of the subject comprising all or a portion of the disease, wherein the disease is cancer and the active agent is an anticancer agent.

14. A process for forming a formulation of thermosensitive anti-cancer agent-containing liposomes, comprising:
dissolving DPPC, DSPG, MSPC, DSPE-PEG2000 and anti-cancer agent at a ratio of about 60-80;6-12:6-12:4-15:1-30 on a weight basis, in organic solvent to form a lipid solution;
removing the organic solvent from said lipid solution to form a dried material;
hydrating the dried material with an aqueous solution of PBS and lactose;
forming a dispersion comprising liposomes and adjusting particle size of said liposomes in dispersion; and
sterilizing said dispersion of liposomes.

15. A process for forming a formulation of thermosensitive anti-cancer agent-containing liposomes, said process comprising:
- dissolving DPPC DSPG, MSPC, and DSPE-PEG2000 in organic solvent;
- removing the organic solvent to form a dried material;
- hydrating the dried material with an aqueous solution to form hydrated lipid material;
- extruding said hydrated lipid material to form a dispersion comprising liposomes;
- adding an anti-cancer agent to said dispersion while heating and mixing to form a dispersion of anti-cancer agent-loaded liposomes
- wherein the DPPC, DSPG, MSPC, DSPE-PEG2000, and the anti-cancer agent are at a ratio of about 60-80:6-12:6-12:4-15:1-30 on a weight basis, and;
- removing excess anti-cancer agent that has not incorporated into said anti-cancer agent-loaded liposomes.

16. The liposomal product formed by the process of claim 14 or claim 15.

* * * * *